| United States Patent [19] | [11] | 4,128,586 |
|---|---|---|
| Ratcliffe | [45] | Dec. 5, 1978 |

[54] CATALYTIC REDUCTION OF AROMATIC SULFONYL HALIDES WITH HYDROGEN SULFIDE TO YIELD AROMATIC THIOLS

[75] Inventor: Charles T. Ratcliffe, Morristown, N.J.

[73] Assignee: Allied Chemical Corporation, Morris Township, Morris County, N.J.

[21] Appl. No.: 881,952

[22] Filed: Feb. 27, 1978

[51] Int. Cl.$^2$ .......................................... C07C 149/28
[52] U.S. Cl. ...................... 260/609 D; 260/302 S; 260/302 F; 260/308 R; 260/608; 544/315; 544/408; 548/337; 548/346; 546/290; 546/179; 546/139
[58] Field of Search ............ 260/609 D, 608, 294.8 R

[56] References Cited

U.S. PATENT DOCUMENTS

| 2,402,641 | 6/1946 | Lazler et al. | 260/609 |
|---|---|---|---|
| 2,792,422 | 5/1957 | Harris et al. | 260/609 D |
| 2,820,780 | 1/1958 | Gutcho et al. | 260/112 |
| 2,986,581 | 5/1961 | Levy et al. | 260/608 |
| 3,994,980 | 11/1976 | Kubicek | 260/609 D |

FOREIGN PATENT DOCUMENTS

| 461101 | 4/1975 | U.S.S.R. | 260/609 D |
|---|---|---|---|

Primary Examiner—Lewis Gotts
Assistant Examiner—Molly C. Eakin
Attorney, Agent, or Firm—Horst M. Kasper

[57] ABSTRACT

A process for reducing aromatic sulfonyl halides with hydrogen sulfide. Hydrogen sulfide is contacted with sulfonyl halides preferably in the presence of a solvent and of a catalyst. The reaction forms thiols and proceeds in the range of between about 50° and 300° C. There is little formation of disulfide and no cleavage of the thiol group.

20 Claims, No Drawings

4,128,586

CATALYTIC REDUCTION OF AROMATIC SULFONYL HALIDES WITH HYDROGEN SULFIDE TO YIELD AROMATIC THIOLS

FIELD OF THE INVENTION

The invention relates to a process for generating thiols from aromatic sulfonyl halides.

BACKGROUND OF THE INVENTION

Hydrogen sulfide is an abundant material today as the by-product from hydrodesulfurization of oil and coal. Chemical synthesis processes employing available hydrogen sulfide as an ingredient are very desirable. It is known that hydrogen sulfide can act as a reducing agent, but, it is much less active than for instance native hydrogen. Therefore, so far as we are aware, the application of hydrogen sulfide has been limited in the past to specific reactions whereas other reactions have not been possible to carry out. For instance U.S. Pat. No. 3,994,980 to Phillips Petroleum Company discloses a process for preparing thiols by contacting a mixture of a carbonyl group containing compound with a sulfur source such as hydrogen sulfide for obtaining thiols. We are unaware of any prior use of hydrogen sulfide for reduction of organic sulfonyl halides. Wilbur A. Lazier et al. in U.S. Pat. No. 2,402,641 discloses the preparation of aryl thiols by hydrogenation of sulfonic acids and of compounds hydrolyzable to these acids with elemental hydrogen.

The preparation of sulfonyl halides is well known for aromatic compounds since the beginnings of the dye and pigment industry.

The selective reduction of aromatic sulfur compounds is frequently difficult and expensive. Direct hydrogenation of an aromatic sulfide, sulfonyl halide or thiol will generally result in cleavage of the sulfur carbon bond to yield hydrogen sulfide and the aromatic group. Presently, the reduction of 2,5-dichlorobenzyl sulfonyl halide is carried out commercially with zinc metal in order to obtain 2,5-dichlorobenzene thiol. In addition to reduction of arene sulfonyl chlorides by various metals, electrolysis is used for such reduction. For instance, benzene sulfonyl chlorides have been reduced with iron and with electrochemical reduction. U.S. Pat. No. 2,820,780 indicates the possibility of reducing organic sulfides to thiols with hydrogen sulfide. Specific examples disclose the reduction of cystline to cysteine and of 2,2-dihydroxy 6,6-dinaphtyl disulfide to two thiol molecules and of glutathione [GSSG] to two thiol molecules [GS].

SUMMARY OF THE INVENTION

It is an object of the present invention to provide a process for reducing aromatic sulfonyl halides to thiols. It is another object of the invention to provide a process for employing hydrogen sulfide in reducing reactions. Aromatic thiols are used in the production of dyes, pigments and pharmaceuticals.

A process is disclosed for reducing aromatic sulfonyl halides to thiols. The reducing agent is hydrogen sulfide and the presence of a cataYst is preferred. Suitable catalysts include sulfur active catalysts such as cobalt, molybdenum, nickel, tungsten and chromium.

DETAILED DESCRIPTION OF THE INVENTION

The present invention discloses the reduction of aryl sulfonyl halides with hydrogen sulfide. Preferably this reduction is accomplished in the presence of a solvent and of a catalyst. Aryl sulfonyl halide includes fluorides, chlorides, bromides and iodides. Preferably, sulfonyl chlorides are employed since they are in general of the lowest cost. Alkyl- and alkoxy- substituents considered in the following are those having straight or branched carbon atom chains with between one and eight carbon atoms such as methyl, ethyl, isopropyl and the like. Aryl sulfonyl halides suitable in the present invention include sufonyl halides of halo-, alkyl-, alkoxy-, and/or aryl derivatives of benzene, naphthalene, phenanthrene, anthracene, pyridine, quinoline, isoquinoline and anthraquinone. Members of this group are the sulfonylhalides of halo-, methyl, ethyl, and/or isopropyl derivatives of benzene. Aryl sulfonyl halides suitable in the present invention include benzene sulfonyl fluoride, benzene sulfonyl chloride, benzene sulfonyl bromide, benzene sulfonyl iodide, o-toluene sulfonyl chloride, p-toluene sulfonyl chloride, 1-naphthalene sulfonyl chloride, 2-naphthalene sulfonyl chloride, 3-pyridine sulfonyl chloride, 6-quinoline sulfonyl chloride, 2-imidazole sulfonyl chloride, 2-benzimidazole sulfonyl chloride, 1,2,4-triazole-3-sulfonyl chloride, 2-thiazole sulfonyl chloride, 2-benzothiazole chloride, 2-pyrimidine sulfonyl chloride, 2-pyrazine sulfonyl chloride, 2,5-dichlorobenzene sulfonyl halide, 2-anthracene sulfonyl chloride, 2-phenanthrene sulfonyl chloride, and the like.

Catalysts suitable in the present invention include sulfur active catalysts. Sulfur active catalysts are materials which upon being sulfided have catalytic properties in hydrodesulfurization reactions. Such catalysts are described by Otto Weiser and Stanislav Landa in "Sulfur Catalysts, Their Properties and Applications" Pergamon Press, Oxford and New York (1973). Such sulfur active catalysts include nickel, tungsten, cobalt, iron, ruthenium, rhodium, iridium, copper, molybdenum, chromium in supported and non-supported state and preferably cobalt-molybdenum, nickel-tungsten and chromium. High surface area supports such as gamma alumina, $SiO_2$ or active carbon can be used.

Preferably the catalysts are presulfidized. The hydrogen sulfide is preferably employed under pressure. Preferably the pressure of the hydrogen sulfide is between about 14 pounds per square inch and 3000 pounds per square inch. The aromatic sulfonyl halide is preferably dissolved in an inert solvent. Such inert solvents include ortho-xylene, toluene, other inert organic solvents such as dichlorobenzene.

The reaction temperature is preferably in the range of between about 50° and 300° C. with a more preferred range of between about 90° to 130° C.

The reaction vessel for the present invention is preferably of such a material which is resistant to hydrogen sulfide, hydrogen chloride, water and their mixtures. Materials and linings for such vessels include polytetrafluoroethylene glass, and inconel. The amount of catalyst employed corresponds to 0.1 parts to 0.0001 parts of the reducible organic compound. The reaction ratio of hydrogen sulfide to sulfonyl chloride employed corresponds to a molar ratio of equal to or greater than 3:1. Preferably, the catalyst is impregnated on active alumina supports. The arrangement of this invention preferably employs a continuous flow of hydrogen sulfide into the system and removal of product hydrogen chloride and water as vapors during the reaction. A countercurrent flow of hydrogen sulfide and aromatic sulfonyl halide can also be employed followed by removal of the thiol on the hydrogen sulfide input side and removal of the hydrogen chloride and water on the aromatic sulfonyl halide input side. Alternatively a back mix reactor can be advantageously used to carry out the reaction. The selectivity of the reaction appears by gas chromatography to be 75% for the thiol made from 2,5-dichlorobenzene sulfonyl chloride. The presence of a solvent like toluene is preferred in order to avoid tar formation with these catalysts.

EXAMPLES

EXAMPLE 1

A sample of Harshaw catalyst number 0603 T ⅛ containing 3% cobalt trioxide and 12% molybdenum trioxide was treated with a 20% stream of hydrogen sulfide at 500° C. for 30 minutes. A cylindrical glass pressure vessel fitted with a polytetrafluoroethylene stop cock was loaded with 1.5 grams of 2,5-dichlorobenzene sulfonyl chloride, 0.15 grams of presulfided cobalt/molybdenum catalysts number 0603 and 15 grams of orthoxylene as a solvent. The stirred mixture was flushed with hydrogen sulfide and connected to a 60 pounds per square inch supply of hydrogen sulfide. After heating the mixture to 110° C. for 17 hours, a clear solution containing black catalyst particles was obtained. The solution was filtered and separated by gas chromatography. A complete conversion of the 2,5-dichlorobenzene sulfonyl chloride was observed. The product consisted of 78.8% 2,5-dichlorobenzene thiol, 2.2% of the disulfide and 21.85 of an unknown component. Subsequent analysis of the sample by combined gas chromatography and chemical ionization mass spectrometry confirmed the thiol and its disulfide as major components. The unknown appeared to be an artifact due to interaction with the 3% Se-30/Gas Chrome column. The solid catalyst residue was analyzed and found to contain 0.31% carbon, 4.89% hydrogen and 4.64% sulfur. The low carbon content of the catalyst indicated little if any coking on the catalyst. Silation of the above sample mixture was also carried out in order to test for higher boiling acids which had not been eluted in the gas chromatography column. A programmed gas chromatographic scan of the mixture revealed no new components. A silated reference of 2,5-dichlorobenzene sulfonic acid was tested and revealed one peak. The retention time did not correspond to any peak observed in the product sample.

EXAMPLE 2

In a similar manner as set forth in Example 1, 1.5 grams of 2,5-dichlorobenzene sulfonyl chloride, 0.15 grams of freshly prepared bismuth sesquisulfide and 16.0 grams of orthoxylene solvent were allowed to react at 110° C. for 17 hours under a hydrogen sulfide pressure of 60 pounds per square inch of hydrogen sulfide. The catalyst was observed to be a bright red color after the reaction in contrast to the black color of bismith sesquioxide. The solution which was filtered and analyzed by gas chromatography showed 72% unreacted 2,5-dichlorobenzene sulfonyl chloride, 23.5% 2,5-dichlorobenzene thiol and 2% 2,5-dichlorobenzene disulfide. The reaction was continued for an additional 3 hours with no change in the product mixture. The decomposition of the catalyst limited the conversion ratio. Analysis of the red solid showed that the active $Bi_2S_3$ had been hydrolyzed by water and hydrogen chloride to yield $Bi_2O_3.2BiCl_3$, a non-catalytic species.

EXAMPLE 3

A reactor tube is packed with 1.0 grams of quartz chips but no catalyst is employed. A 10% solution of 2,5-dichlorobenzene sulfonyl chloride is fed into the reactor at a rate of 12.6 g per hour with a gas flow of 30 ccm/min. of hydrogen sulfide and 50 ccm/min. of nitrogen. The bed is held at a temperature of 300° C. The product being collected from the base of the reactor at 20 minute intervals shows a 20-30% conversion of 2,5-dichlorobenzene sulfonyl chloride at a calculated contact time of 0.24. The products are 2,5-dichlorobenzene thiol and its corresponding disulfide. An increase in temperature results in increasing amounts of coke and tar formation.

I claim:

1. A process for reducing aromatic sulfonyl halides comprising
   contacting the sulfonyl halide with hydrogen sulfide for producing reduced derivatives of the sulfonyl halide.

2. The process as set forth in claim 1 comprising separating the reduced derivative of the sulfonyl halide.

3. The process as set forth in claim 1 comprising
   contacting the sulfonyl halide and the hydrogen sulfide with a catalyst.

4. The process as set forth in claim 3 wherein the catalyst is a sulfur active catalyst.

5. The process as set forth in claim 3 wherein the catalyst is a nickel tungsten containing catalyst.

6. The process as set forth in claim 3 wherein the catalyst is a chromium containing catalyst.

7. The process as set forth in claim 3 wherein the catalyst is a cobalt molybdenum containing catalyst.

8. The process as set forth in claim 1 wherein the catalyst includes a member of the group Co, Mo, Ni, W, Cu, Fe, Ru, Rh, Ir or mixtures thereof.

9. The process as set forth in claim 1 wherein the hydrogen sulfide pressure is greater than 100 Torr.

10. The process as set forth in claim 1 wherein the contacting is at a temperature of between about 50° C. and 300° C.

11. The process as set forth in claim 1 wherein the contacting is at a temperature of between about 90° C. and 130° C.

12. The process as set forth in claim 1 wherein the halide is a chloride.

13. The process as set forth in claim 1 wherein the aromatic sulfonyl halide is dissolved in an inert solvent.

14. The process as set forth in claim 13 wherein the solvent is a member of the group consisting of benzene, toluene, xylene, chlorobenzene and chlorotoluene.

15. The process as set forth in claim 1 wherein continuously $H_2S$ flows into a system and HCl and $H_2O$ vapors are removed.

16. The process as set forth in claim 1 wherein the reaction is carried out in a back mix reactor.

17. The process as set forth in claim 1 wherein the aromatic sulfonyl halide is a halo, alkyl, alkoxy and/or aryl derivative of a member of the group consisting of benzene-, naphthalene-, phenanthrene-, anthracene-, pyridine-sulfonyl halide.

18. The process as set forth in claim 17 wherein the aromatic sulfonyl halide is a halo, methyl, ethyl and/or isopropyl derivative of benzene-sulfonyl halide.

19. The process as set forth in claim 18 wherein the aromatic sulfonyl halide is 2,5-dichlorobenzene sulfonyl chloride.

20. The process as set forth in claim 1 wherein the reduced derivative is a thiol.